United States Patent [19]

King et al.

[11] Patent Number: 5,873,887
[45] Date of Patent: Feb. 23, 1999

[54] BLOOD SAMPLING DEVICE

[75] Inventors: Toby King; Anne Miller, both of Cambridge, United Kingdom

[73] Assignee: Bayer Corporation, Pittsburgh, Pa.

[21] Appl. No.: 735,975

[22] Filed: Oct. 25, 1996

[51] Int. Cl.⁶ ................................................ A61B 17/34
[52] U.S. Cl. ............................................ 606/182; 128/770
[58] Field of Search .................................. 606/181, 182, 606/183; 128/765, 766, 770

[56] References Cited

U.S. PATENT DOCUMENTS

| | | |
|---|---|---|
| Re. 32,922 | 5/1989 | Levin et al. . |
| 4,442,836 | 4/1984 | Meinecke et al. . |
| 4,449,529 | 5/1984 | Burns et al. . |
| 4,462,405 | 7/1984 | Ehrlich . |
| 4,517,978 | 5/1985 | Levin et al. . |
| 4,553,541 | 11/1985 | Burns . |
| 4,653,513 | 3/1987 | Dombrowski . |
| 4,858,607 | 8/1989 | Jordan et al. . |
| 4,976,724 | 12/1990 | Nieto et al. . |
| 5,201,324 | 4/1993 | Swierczek . |
| 5,368,047 | 11/1994 | Suzuki et al. . |

*Primary Examiner*—Gary Jackson
*Assistant Examiner*—William Lewis
*Attorney, Agent, or Firm*—Roger N. Coe

[57] ABSTRACT

An automatic blood sampling device is provided with a housing (12, 14, 18, 20), a reciprocable shaft (50) disposed in the housing (12, 14, 18, 20), and a lancet (40) operatively coupled to the shaft (50). The lancet (40) is movable between a retracted position in which the lancet (40) is disposed within the housing (12, 14, 18, 20) and an extended position in which the lancet (40) extends outside of the housing (12, 14, 18, 20).

The blood sampling device includes means for retaining the lancet (40) in its retracted position, means (51) for causing the lancet (40) to automatically move from its retracted position to its extended position, and means for generating a reduced internal pressure within an area in the housing (12, 14, 18, 20) as the lancet (40) moves from its retracted position to its extended position to facilitate drawing blood from a skin puncture to be made by the lancet (40) into an interior portion of the housing (12, 14, 18, 20), the internal pressure being less than the ambient pressure outside of the housing (12, 14, 18, 20) of the sampling device.

20 Claims, 2 Drawing Sheets

BLOOD SAMPLING DEVICE

BACKGROUND OF THE INVENTION

The present invention relates to a blood sampling device that incorporates a lancet for piercing the skin and creates a partial vacuum to enhance recovery of a sample of blood.

Various types of blood sampling devices for drawing a blood sample from a skin puncture made by a lancet have been described. For example, U.S. Pat. No. 5,368,047 to Suzuki, et al. discloses a blood sampling device that has a lancet connected to a spring-loaded plunger that is reciprocable in a cylindrical housing between a retracted position and an extended position. The plunger has a gasket which makes sealing contact with the interior wall of the housing when the plunger is moved from its extended position to its retracted position.

In the operation of the Suzuki, et al. device, the plunger is pushed to its retracted position by the user and then placed against the skin from which the blood sample is to be drawn. Upon being released, the plunger is urged to travel from its retracted position to its extended position via a spring. When the plunger reaches its fully extended position, the lancet punctures the skin. After the skin is punctured, the plunger moves back to its retracted position, during which movement the pressure inside the housing is reduced due to the sliding engagement of the gasket against the interior wall of the housing. This reduced pressure, which is in contact with the skin puncture, enhances passage of blood from the puncture into the blood sampling device.

SUMMARY OF THE INVENTION

The invention is directed to an automatic blood sampling device that is relatively painless and simple to use. The blood sampling device has a housing, a reciprocable shaft disposed in the housing, and a lancet operatively coupled to the shaft. The lancet is movable between a retracted position in which the lancet is disposed within the housing and an extended position in which the lancet extends outside of the housing.

The blood sampling device includes means for retaining the lancet in its retracted position, means for causing the lancet to automatically move from its retracted position to its extended position, and means for generating a reduced internal pressure within the housing as the lancet moves from its retracted position to its extended position to facilitate drawing blood from a skin puncture to be made by the lancet. The reduced internal pressure in the housing of the sampling device is less than the ambient pressure outside the sampling device.

The means for generating the reduced internal pressure within the housing may comprise a bore having a substantially air-tight end and a plunger connected to the shaft. The plunger has an exterior portion which makes sealing contact with the bore so that the reduced internal pressure is formed within the bore when the plunger is moved in a direction away from the air-tight end of the bore. The means for retaining the lancet in its retracted position may be a latch mechanism, and the means for causing the lancet to automatically move from its retracted position to its extended position may be a spring.

The blood sampling device may also include means for venting the reduced internal pressure area within the sampling device to the outside atmosphere, means for decelerating the lancet as the lancet moves towards its extended position, and/or a check valve in fluid communication with the acceleration chamber to allow air to pass from the acceleration chamber to a point outside the housing of the sampling device.

These and other features and advantages of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENTS

Figure 1:
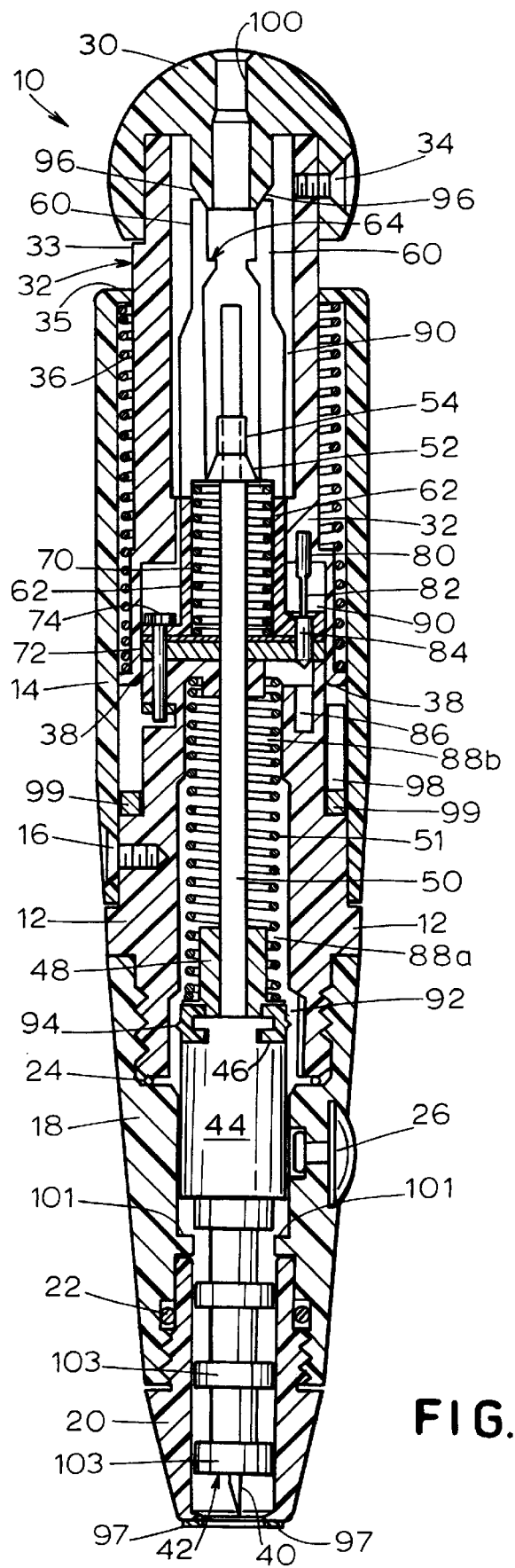
FIG. 1 is a cross-sectional view of one embodiment of a blood sampling device in accordance with the invention.

FIG. 1 is a cross-sectional view of a first embodiment of a blood sampling device 10 for taking a sample of blood from a patient. Referring to FIG. 1, the blood sampling device 10 has a housing composed of a main body 12, an upper housing portion 14 connected to the main body 12 via a screw 16, a lower housing portion in the form of a sleeve 18 threadably connected to the main body 12, and an end cap 20 threadably connected to the sleeve 18. An O-ring 22 is disposed between the end cap 20 and the sleeve 18 to provide an air-tight seal between those two components 18, 20, and an O-ring 24 is disposed between the sleeve 18 and the main body 12 to provide an air-tight seal between those two components 12, 18. A conventional one-way check valve 26 is disposed in a bore formed in the sleeve 18 to allow air to escape from the interior of the blood sampling device 10 to the outside and to prevent air from passing into the interior of the sampling device 10.

The blood sampling device 10 has an actuator mechanism composed of a semi-spherical knob 30 attached to an actuator 32 via a screw 34. The actuator 32 may be provided with a relatively narrow, outwardly extending key portion 33 which is disposed within a slot (not shown) in an upper surface 35 of the housing portion 14 to prevent rotation of the actuator 32 relative to the housing portion 14. The knob 30 and the actuator 32 are biased downwardly via a helical spring 36 disposed between the upper surface 35 of the housing portion 14 and an annular flange 38 that extends outwardly from the bottom of the actuator 32.

A lancet assembly composed of a lancet 40 and a lancet shaft 42 is disposed in the interior portion of the blood sampling device 10. The lancet shaft 42 is connected to a cylindrical lancet holder 44, and the lancet holder 44 is connected to a plunger assembly composed of an annular rubber plunger 46 connected to a plunger hub 48. The plunger hub 48 is connected to an elongate shaft 50, and a helical spring 51 is disposed between the plunger hub 48 and an upper internal surface of the main body 12.

Figure 3:
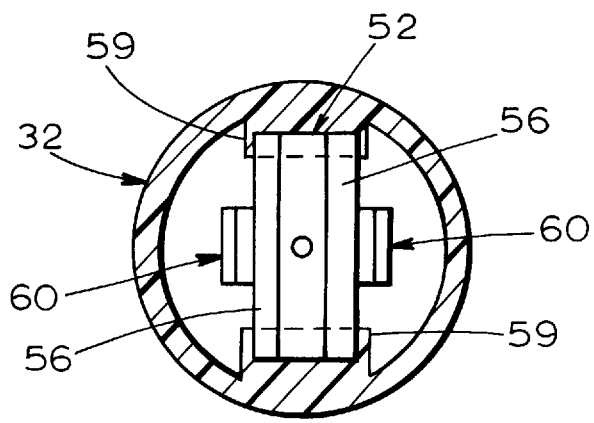
FIG. 3 is a cross-sectional view of the blood sampling device taken along lines 3—3 shown in FIG. 2 with portions of the blood sampling device omitted for sake of clarity.
Figure 4:
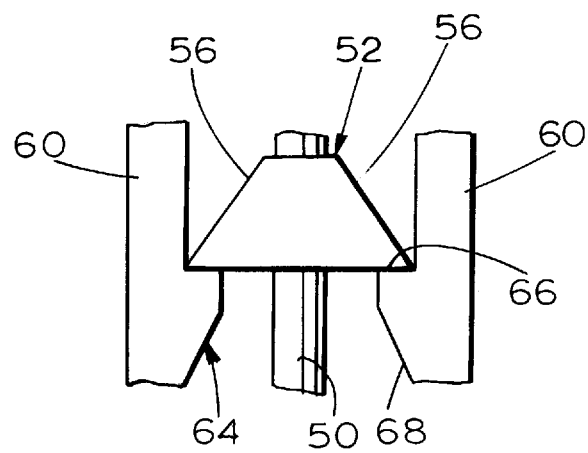
FIG. 4 is a side view of a latch mechanism of the blood sampling device.

The shaft 50 has a latch 52 connected to it via a nut 54 at a fixed position near the upper end of the shaft 50. The latch 52 is adapted to selectively spread apart and engage a plurality of upwardly extending retaining arms 60 of a retainer member 62. FIG. 3 illustrates of the latch 52 and the retaining arms 60, and FIG. 4 is an enlarged side view of the latch 52 and portions of the retaining arms 60. Referring to FIGS. 3 and 4, the latch 52 has a pair of angled spreading surfaces 56 and is adapted to selectively engage a pair of outwardly extending flanges 59 (FIG. 3) integrally formed with the actuator 32. A ledge 64 is formed on each of interior sides of the retaining arms 60. Each ledge 64 has a horizontally disposed retaining surface 66 and a diagonally sloped spreading surface 68.

When in the position shown in FIG. 1, the latch 52 rests on top of a thin annular washer which is disposed on top of a helically coiled spring 70. The spring 70 is supported by a sealing assembly composed of a steel washer 71 (FIG. 5) and a sealing member 72. The sealing assembly and the retaining member 62 are connected to the main body 12 via a bolt assembly 74.

Figure 5:
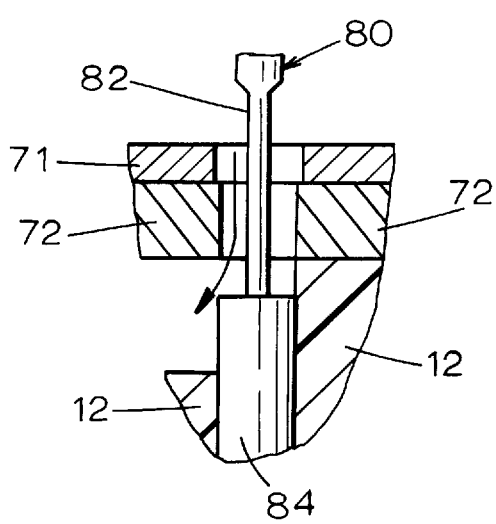
FIG. 5 is a side view of a venting assembly of the blood sampling device.

Referring to FIGS. 1 and 5, a venting peg 80 is connected to the actuator 32. The venting peg 80 has a middle cylindrical portion 82 having a relatively small diameter and a bottom portion 84 having a relatively large diameter. The venting peg 80 is movable through a bore formed in the bottom of the retainer 62, an aligned bore formed in the steel washer 71 (FIG. 5), and an aligned bore (FIG. 5) formed in the sealing member 72.

When the actuator 32 is forced downwardly, the bottom portion 84 of the venting peg 80 passes into a cylindrical well 86 formed in the main body 12 so that the relatively thin portion 82 of the venting peg 80 is disposed within the aligned bores formed in the members 71, 72. Thus, an air passageway may be selectively formed from a lower internal chamber 88 referred to as a suction chamber to an upper internal chamber 90. The chamber 90 is in fluid communication with the outside due to an annular space formed between the actuator 32 and the surface 35 of the upper housing portion 14. Air may flow through the air passageway between the chambers 88, 90 as indicated by the arrow in FIG. 5.

A cylindrical internal chamber 92 referred to as an acceleration chamber is formed coaxially with the suction chamber 88. The diameter of the acceleration chamber 92 is slightly larger than that of the suction chamber 88. The rubber plunger 46 has an annular portion 94 having a slightly enlarged diameter. The diameter of the annular portion 94 is slightly greater than the internal diameter of a portion 88a of the suction chamber 88 and less than the internal diameter of the acceleration chamber 92. Consequently, when the rubber plunger 46 is moving within the suction chamber portion 88a, substantially no air passes through the air-tight seal formed by the abutment of the annular portion 94 with the internal surface of the suction chamber portion 88a. The suction chamber 88 is provided with an upper portion 88b which is slightly reduced in diameter to minimize the dead volume of the suction chamber 88.

To use the sampling device 10 to draw a blood sample, the user first pulls the knob 30 upwardly from its position shown in FIG. 1. As the knob 30 and the actuator 32 to which it is attached move upwardly, the top surfaces of the flanges 59 on the actuator 32 make contact with the bottom surface of the latch 52. As the knob 30 continues its upward movement, the flanges 59 force the latch 52 upwardly, which causes the shaft 50, the plunger 46, the lancet holder 44 and the lancet shaft 42 to move upwardly as well.

Figure 2:
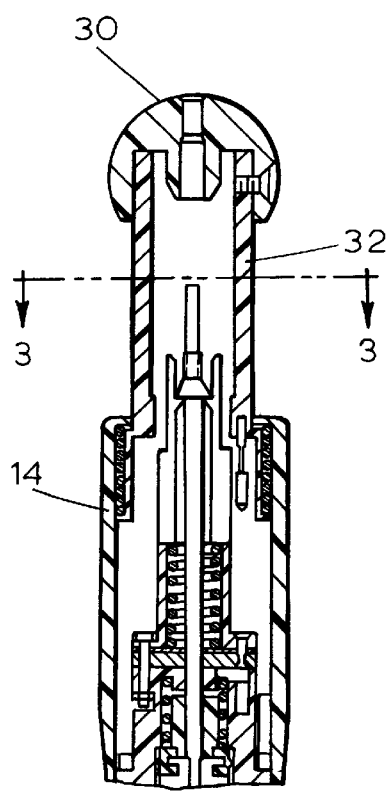
FIG. 2 is a cross-sectional view of a portion of the blood sampling device shown in a ready position.

As the knob 30 and the latch 52 continue moving upwardly, the angled spreading surfaces 56 on the latch 52 abut the angled spreading surfaces 68 on the ledges 64 of the retaining members 60 and force the retaining members 60 apart. When the latch 52 is moved upwardly past the ledges 64, the resilient retaining members 60 snap inwardly so that downward movement of the latch 52 is prevented due to the ledges 64. FIG. 2 illustrates the sampling device 10 when the latch 52 is supported by the ledges 64 of the retaining members 60.

When the user hears the audible click generated by the retaining members 60 snapping against the latch 52, the user knows that the sampling device 10 is in a retracted, ready state. A bore 100 may optionally be formed in the knob 30 so that the user can visually determine that the sampling device is in the ready state by seeing the top end of the shaft 50 in the bore 100. The user then allows the knob 30 to be moved downwards, under the influence of the spring 36 (which is optional), until a pair of angled surfaces 96 on the internal underside of the knob 30 abut the top angled surfaces of the retaining members 60 (as shown in the upper portion of FIG. 1).

When the sampling device 10 is in the ready state, the lancet shaft 42, the lancet holder 44, and the plunger 48 are in a retracted position located a relatively large distance inwardly from the bottom end of the sampling device 10, and the spring 51 is compressed to a relatively large degree. Also, the enlarged annular portion 94 of the rubber plunger 96 is positioned within the suction chamber 88 at a point near the top of the suction chamber portion 88a.

To draw the blood sample, the user first positions the bottom end of the sampling device 10 firmly against the skin where the blood sample is to be taken so that a relatively airtight seal is formed between the bottom end of the sampling device and the skin. To facilitate the formation of an airtight seal, an annular rubber washer or sealing member 97 may be provided on the bottom of the end cap 20, and the sealing member 97 may be wetted. Alternatively, the bottom of the end cap 20 may be provided with an annular lip to effect the seal.

With the sampling device 10 pressed against the skin, the user then forces the knob 30 downwards until the annular flange 38 on the bottom of the actuator 32 makes contact with a relatively stiff spring 98 supported by an annular spring holder 99, at which point the angled surfaces 96 on the knob 30 have spread apart the retaining members 60 to a sufficient extent so that the latch 52 is released by the ledges 64. When that occurs, the bore in the sealing member 72 will be sealed by the relatively large bottom portion 84 of the venting peg 80 so that the upper end of the suction chamber 88 is substantially airtight.

When the latch 52 is released, the compressed spring 51 will force the plunger hub 48, the lancet holder 44, and the lancet shaft 42 downwardly. As the plunger hub 48 moves downwardly, the downward movement of the enlarged portion 94 of the rubber plunger 46 within the suction chamber portion 88a will cause a reduced air pressure or partial vacuum within the suction chamber 88 since air cannot enter the suction chamber 88 from other points.

It should be noted that the acceleration of the lancet holder 44 and lancet shaft 42 is somewhat damped when the plunger 46 is moving within the suction chamber portion 88a since the partial vacuum being formed within the suction chamber 88 will exert an upward force on the lancet holder 44 (the friction from the annular portion 94 will also damp the acceleration). The acceleration of the lancet holder 44 and lancet shaft 42 is not damped due to a positive pressure buildup in the internal portions of the sampling device 10 below the suction chamber 88 since any excess air pressure is vented out of the sampling device 10 via the one-way check valve 26.

When the enlarged portion 94 of the rubber plunger 46 passes from the suction chamber portion 88a to the larger acceleration chamber 92, the rate of acceleration of the lancet holder 44 and lancet shaft 42 will increase due to: 1) decreased friction generated by the rubber plunger 46 since the enlarged portion 94 of the plunger 46 no longer makes significant contact with any internal surface of the sampling device 10, and 2) the equalization of air pressures above and below the plunger 46.

With respect to 2), it should be noted that, when the plunger 46 passes from the suction chamber portion 88a to the acceleration chamber 92, the partial vacuum formed in the suction chamber 88 will be somewhat reduced by air entering the suction chamber 88 from below the plunger 46. However, a partial vacuum will still exist within the sampling device 10 since no air enters the lower interior portion of the sampling device 10 from the outside.

The lancet holder 44 and lancet shaft 42 continue to accelerate until the latch 52 makes contact with the annular disk support by the spring 70, at which point the spring 70 starts to decelerate the lancet holder 44 and lancet shaft 42. The lancet holder 44 and lancet shaft 42 move downwardly until the bottom surface of the lancet holder 44 makes contact with an annular stopping flange 101 integrally formed on the interior of the sleeve 18. The depth of the skin puncture made by the lancet 40 may be adjusted within a range, for example, of 0.5 millimeters to 2.5 millimeters by rotating the end cap 20, which rotation varies the distance between the bottom of the end cap 20 and the stopping flange 101.

When the lancet 40 pierces the skin, blood will be drawn into the bottom end of the sampling device 10 due to the partial vacuum formed therein. After the skin is punctured, the lancet 40 is retracted back into the sampling device 10 by the spring 70, which forces the lancet holder 44 and lancet shaft 42 upwards. Blood will be drawn into the sampling device 10 until the user vents the sampling device 10 to eliminate the partial vacuum. The partial vacuum may have a magnitude of approximately 0.5 Bar below atmospheric pressure. To achieve that partial vacuum, the dead volume around the lancet should be minimized. One or more enlarged annular flanges 103 may be formed on the lancet holder 42 to reduce the internal volume within the bottom end of the sampling device 10. Alternatively, the lancet holder 42 may be provided with a larger, constant diameter to reduce the dead volume within the sampling device.

The sampling device of FIG. 1 is vented by the user by pressing the knob 30 downwards against the relatively stiff spring 98 so that the venting plug 80 occupies the position shown in FIG. 5. When that occurs, air will flow from the upper interior portion of the sampling device 10 into the lower interior portion of the sampling device 10 where the partial vacuum exists. It should be noted that the upper interior portion of the sampling device 10 is in fluid communication with the outside due to an annular space formed between the actuator 32 and the surface 35 of the upper housing portion 14.

Figure 6:
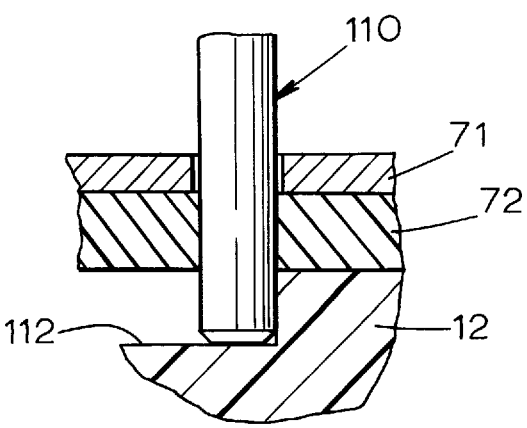
FIG. 6 is a side view of an alternative embodiment of a venting assembly.

A portion of an alternative embodiment of the sampling device 10 is illustrated in FIG. 6. The alternative sampling device utilizes a different mode of venting the interior of the sampling device 10 after the blood sample is drawn. Unless otherwise indicated below in connection with FIG. 6, the features of the alternative sampling device are identical to those of the sampling device 10 described above in connection with FIGS. 1–4.

Referring to FIG. 6, the alternative sampling device utilizes a constant-diameter venting peg 110 that is connected to the bottom portion of the actuator 32. The venting peg 110 is movable between a non-venting position (shown in FIG. 6) in which it blocks the bore formed in the sealing member 72 and a venting position in which the venting peg 110 is disposed above the bore in the sealing member 72 so that air may vent through the bores. When the venting peg 110 is in its non-venting position, its bottom end abuts an end stop, which may be in the form of a horizontal interior surface 112 of the main body 12 (the cylindrical well 86 of FIG. 1 is eliminated). Alternatively, the end stop may be composed of a harder material.

In the alternative sampling device, the spring 98 must be stronger than the actuator return spring 36 so that the venting peg 110 is normally held in its venting position above the bore in the sealing member 72. The length of the venting peg 110 is selected so that the latch 52 is not released by the retaining arms 30 until the venting peg 110 reaches its non-venting position.

To operate the alternative sampling device, after the latch 52 was released by the retaining members 30, the user would gently force the knob 30 downwardly against the force of the spring 98 to keep the venting peg 110 in its non-venting position while the blood sample was being withdrawn. To vent the device, the user would simply release the knob 30, so that the spring 98 would force the venting peg 110 upwards from its non-venting position to its venting position. This alternative sampling device may be preferred since the construction of the venting peg is simplified and since a relatively large force is required to vent the sampling device of FIG. 1 to prevent accidental venting.

Modifications and alternative embodiments of the invention will be apparent to those skilled in the art in view of the foregoing description. This description is to be construed as illustrative only, and is for the purpose of teaching those skilled in the art the best mode of carrying out the invention.

The details of the structure and method may be varied substantially without departing from the spirit of the invention, and the exclusive use of all modifications which come within the scope of the appended claims is reserved.

What is claimed is:

1. A blood sampling device, comprising:
   a housing (12, 14, 18, 20);
   a shaft (50) disposed in said housing (12, 14, 18, 20);
   a lancet (40) operatively coupled to said shaft (50), said lancet (40) being movable between a retracted position in which said lancet (40) is disposed within said housing (12, 14, 18, 20) and an extended position in which said lancet (40) extends outside of said housing (12, 14, 18, 20);
   means (50, 52, 60, 64) for retaining said lancet (40) in said retracted position;
   means (51) for causing said lancet (40) to automatically move from said retracted position to said extended position; and
   means for generating a reduced internal pressure within an area in said housing (12, 14, 18, 20) as said lancet (40) moves from said retracted position to said extended position to facilitate drawing blood from a skin puncture to be made by said lancet (40) into an interior portion of said housing (12, 14, 18, 20), said internal pressure being less than an ambient pressure outside of said housing (12, 14, 18, 20), said means for generating a reduced internal pressure comprising:

a suction chamber (88) disposed in said housing (12, 14, 18, 20), said suction chamber (88) having a diameter and a substantially air-tight end;

an acceleration chamber (92) disposed in said housing (12, 14, 18, 20) and being disposed generally coaxially with said suction chamber (88), said acceleration chamber (92) having a diameter larger than said diameter of said suction chamber (88); and a plunger (46) connected to said shaft (50), said plunger (46) having an exterior portion (94) which makes sealing contact with said suction chamber (88) so that said reduced internal pressure is formed within said suction chamber (88) when said plunger (46) is moved in a direction away from said substantially air-tight end of said suction chamber (88), said exterior portion (94) of said plunger (46) having a diameter smaller than said diameter of said acceleration chamber (92) to facilitate acceleration of said shaft (50) towards said extended position.

2. A device as defined in claim 1 wherein said means (50, 52, 60, 64) for retaining said lancet (40) in said retracted position comprises a latch mechanism (52).

3. A device as defined in claim 1 wherein said means for causing said lancet (40) to automatically move from said retracted position to said extended position comprises a spring (51).

4. A device as defined in claim 1 additionally comprising means (80) for venting said reduced internal pressure area to increase said reduced internal pressure.

5. A device as defined in claim 1 additionally comprising means (70) for decelerating said lancet (40) as said lancet (40) moves towards said extended position.

6. A device as defined in claim 1 additionally comprising a check valve (26) in fluid communication with said acceleration chamber (92) to allow air to pass from said acceleration chamber (92) to a point outside of said housing (12, 14, 18, 20).

7. A blood sampling device, comprising:

a housing (12, 14, 18, 20);

a shaft (50) disposed in said housing (12, 14, 18, 20);

a lancet (40) operatively coupled to said shaft (50), said lancet (40) being movable between a retracted position in which said lancet (40) is disposed within said housing (12, 14, 18, 20) and an extended position in which said lancet (40) extends outside of said housing (12, 14, 18, 20);

means (50, 52, 60, 64) for retaining said lancet (40) in said retracted position;

means (51) for causing said lancet (40) to automatically move from said retracted position to said extended position; and means for generating a reduced internal pressure within an area in said housing (12, 14, 18, 20) as said lancet (40) moves from said retracted position to said extended position to facilitate drawing blood from a skin puncture to be made by said lancet (40) into an interior portion of said housing (12, 14, 18, 20), said internal pressure being less than an ambient pressure outside of said housing (12, 14, 18, 20).

8. A device as defined in claim 7 wherein said housing (12, 14, 18, 20) comprises a first housing portion, a second housing portion connected to said first housing portion, and an end cap connected to said second housing portion.

9. A device as defined in claim 7 wherein said means (50,52,60,64) for retaining said lancet (40) in said retracted position comprises a latch mechanism (52).

10. A device as defined in claim 7 wherein said means (51) for causing said lancet (40) to automatically move from said retracted position to said extended position comprises a spring (51).

11. A device as defined in claim 7 additionally comprising means (80) for venting said reduced internal pressure area to increase said reduced internal pressure.

12. A device as defined in claim 7 additionally comprising means (70) for decelerating said lancet (40) as said lancet (40) moves towards said extended position.

13. A device as defined in claim 7 additionally comprising a check valve (26) in fluid communication with an acceleration chamber (92) to allow air to pass from said acceleration chamber (92) to a point outside of said housing (12, 14, 18, 20).

14. A blood sampling device, comprising:

a housing (12, 14, 18, 20);

a shaft (50) disposed in said housing (12, 14, 18, 20);

a lancet (40) operatively coupled to said shaft (50), said lancet (40) being movable between a retracted position in which said lancet (40) is disposed within said housing (12, 14, 18, 20) and an extended position in which said lancet (40) extends outside of said housing (12, 14, 18, 20);

means (50, 52, 60, 64) for retaining said lancet (40) in said retracted position;

means (51) for causing said lancet (40) to automatically move from said retracted position to said extended position; and means for generating a reduced internal pressure within an area in said housing (12, 14, 18, 20) as said lancet (40) moves from said retracted position to said extended position to facilitate drawing blood from a skin puncture to be made by said lancet (40) into an interior portion of said housing (12, 14, 18, 20), said internal pressure being less than an ambient pressure outside of said housing (12, 14, 18, 20), said means for generating a reduced internal pressure comprising:

a bore (88) disposed in said housing (12, 14, 18, 20) and having a substantially air-tight end; and a plunger (46) connected to said shaft (50), said plunger (46) having an exterior portion (94) which makes sealing contact with said bore (88) so that said reduced internal pressure is formed within said bore (88) when said plunger (46) is moved in a direction away from said air-tight end of said bore (88).

15. A device as defined in claim 14 wherein said housing (12, 14, 18, 20) comprises a first housing portion, a second housing portion connected to said first housing portion, and an end cap connected to said second housing portion.

16. A device as defined in claim 14 wherein said means (50, 52, 60, 64) for retaining said lancet (40) in said retracted position comprises a latch mechanism (52).

17. A device as defined in claim 14 wherein said means (51) for causing said lancet (40) to automatically move from said retracted position to said extended position comprises a spring (51).

18. A device as defined in claim 14 additionally comprising means (80) for venting said reduced internal pressure area to increase said reduced internal pressure.

19. A device as defined in claim 14 additionally comprising means (70) for decelerating said lancet (40) as said lancet (40) moves towards said extended position.

20. A device as defined in claim 14 additionally comprising a check valve (26) in fluid communication with said acceleration chamber (92) to allow air to pass from said acceleration chamber (92) to a point outside of said housing (12, 14, 18, 20).

* * * * *